US006277781B1

(12) United States Patent
Commereuc et al.

(10) Patent No.: US 6,277,781 B1
(45) Date of Patent: Aug. 21, 2001

(54) PROCESS FOR PREPARING A RHENIUM AND CESIUM BASED METATHESIS CATALYST

(75) Inventors: Dominique Commereuc, Meudon; François Hugues, Vernaizon; Lucien Saussine, Croissy sur Seine, all of (FR)

(73) Assignee: Institut Francais du Petrole, Rueil-Malmaison (FR)

( * ) Notice: Subject to any disclaimer, the term of this patent is extended or adjusted under 35 U.S.C. 154(b) by 0 days.

(21) Appl. No.: 09/413,192

(22) Filed: Oct. 5, 1999

(30) Foreign Application Priority Data

Oct. 5, 1998 (FR) .................................................. 98 12469

(51) Int. Cl.[7] .............................. B01J 23/04; B01J 23/36
(52) U.S. Cl. ........................................... 502/344; 502/300
(58) Field of Search .................................... 502/300, 344, 502/355

(56) References Cited

U.S. PATENT DOCUMENTS

| 3,658,927 | * | 4/1972 | Crain et al. . | |
| 4,412,089 | | 10/1983 | Mulder et al. | 585/645 |
| 4,795,734 | * | 1/1989 | Chauvin et al. . | |
| 4,880,763 | | 11/1989 | Eri et al. | 502/302 |
| 5,449,852 | * | 9/1995 | Chauvin et al. . | |
| 5,750,790 | | 5/1998 | King et al. | 564/469 |

FOREIGN PATENT DOCUMENTS

| 0 268 525 | 5/1988 | (EP) . |
| 0 838 449 | 4/1998 | (EP) . |

OTHER PUBLICATIONS

XP–002105315—Metathesis of n–Alkenes Over a $CsNO_3–Re_2O_7–Al_2O_3$ Catalyst, Journal of Molecular Catalysis, vol. 46 (1988) pp. 157–172.

* cited by examiner

*Primary Examiner*—Steven P. Griffin
*Assistant Examiner*—Christina Ildebrando
(74) *Attorney, Agent, or Firm*—Millen, White, Zelano & Branigan, P.C.

(57) ABSTRACT

The present invention provides a catalyst and a process for metathesis of olefinic $C_4$ cuts. The catalyst contains rhenium, cesium and delta alumina. The preferred catalyst contains at least one rhenium compound deposited on a support principally composed of alumina, treated at a temperature of more than 750° C., and modified by at least one cesium compound. With the use of the catalyst, the duration of the cycle between two regeneration operations can be substantially increased. The catalyst is suitable for use in a process for production of propylene from an olefinic $C_4$ cut in three steps: (1) selective hydrogenation of butadiene with isomerisation of 1-butene to 2-butene, (2) separation by distillation of the major portion of the isobutene, and (3) metathesis of the cut rich in 2-butene with ethylene.

20 Claims, No Drawings

PROCESS FOR PREPARING A RHENIUM AND CESIUM BASED METATHESIS CATALYST

The invention relates to a catalyst comprising (and preferably constituted by) delta alumina, rhenium and cesium, and to a process for preparing the catalyst. The invention also relates to a metathesis process using this catalyst, and more particularly to a process for metathesis of an olefinic $C_4$ cut (i.e. a cut containing butenes).

In one particular aspect, the present invention relates to a process for converting a $C_4$ hydrocarbon cut containing isobutene, after selective hydrogenation of butadiene and acetylenic compounds and hydroisomerization of 1-butene to 2-butene, by metathesis with ethylene in the presence of a catalyst based on rhenium improved by the incorporation of cesium and by the presence of delta alumina.

Cracking light paraffins produces ethylene and propylene required for petrochemistry. It also produces a certain number of other products including a $C_4$ hydrocarbon cut which principally contains butadiene, isobutene, n-butenes and butanes, also traces of acetylenic hydrocarbons.

The metathesis reaction converts such cuts, which are often inadequately used, to compounds with a higher intrinsic value. As an example, metathesis with ethylene of an olefinic $C_4$ cut, which has already undergone selective hydrogenation of butadiene and acetylenic compounds and hydroisomerization of 1-butene to 2-butene, can produce propylene.

When such a reaction is carried out using the usual rhenium-based metathesis catalysts, with a $C_4$ cut containing isobutene, this partially polymerizes on contact with the catalyst and that secondary reaction causes a large reduction in the duration of the cycle for the catalyst between two regeneration operations.

Incorporating cesium into a rhenium-based metathesis catalyst has been described in French patent FR-A-2 373 504, for the preparation of branched olefins. In United States patent U.S. Pat. No. 5 057 644, cesium has been cited as a possible additional alkaline element in a catalyst activated at 300–600° C. brought into the presence of organic borane as a promoter. FR-A-I 572 314 indicates that the selectivity of a metathesis catalyst can be increased by adding cesium in particular, and that activation occurs at 300–750° C.

The alumina used as a support in the prior art is generally a gamma alumina and the catalyst is heat activated in a temperature range which usually does not exceed 750° C., although U.S. Pat. No. 3,594,440 indicates that it is possible to go up to 900° C., with no mention of a particular advantage. In a more recent publication, it is indicated that there is no interest in activating a cesium-rhenium-alumina catalyst at a temperature of more than 300° C., the catalyst being prepared by impregnating rhenium into alumina, calcining at 550° C., introducing cesium by impregnation, calcining at 500° C., then activating in nitrogen (T. Kawai et al., Journal of Molecular Catalysis, vol. 76, pp. 249–261, 1992).

We have now discovered that the use of a rhenium- and cesium-based catalyst which prior to the reaction has been treated at a temperature of more than 750° C., generally at most 1000° C., leads to a substantial reduction in the deactivation rate, without substantially affecting the activity for the it metathesis reaction, for example, which substantially increases the duration of cycles between two regeneration steps.

Without wishing to be bound by a particular interpretation, heat activation of a gamma alumina at temperatures beyond 750° C., and generally of at most 1000° C., is known to partially transform it into delta alumina. The beneficial effect on performance could be considered to be attributed to the presence of this type of alumina combined with the presence of cesium.

The catalyst used in the process of the invention thus comprises (and is preferably constituted by) at least three components:

a porous alumina-based support; more generally, the support is principally composed by alumina, and advantageously it contains at least 75% by weight of alumina, preferably it is constituted by alumina, with at least a portion of the alumina being delta alumina (at least 0.5% by weight and preferably at least 1% by weight, or more preferably, 5% by weight and preferably 5–50% by weight)

0.01% to 20% by weight of rhenium;

and 0.01% to 5% by weight of cesium.

The present invention also concerns a process for preparing said catalyst. In this process, a catalyst precursor based on (gamma alumina and rhenium is formed and said precursor undergoes heat treatment at more than 750° C. in a non-reducing gas atmosphere. In one implementation, the precursor also contains cesium. In a preferred implementation, the precursor containing rhenium but not cesium, which has been heat treated at more than 750° C., is impregnated with a cesium compound, dried than activated.

The porous starting support is based on gamma alumina, and preferably contains at least 75% by weight of alumina, and advantageously has an appreciable surface area, for example at least 10 $m^2/g$, and preferably at least 50 $m^2/g$, and a sufficient pore volume, for example at least 0.1 ml/g, preferably 0.3–1 ml/g.

The rhenium compound can be introduced into the support, for example by vapour phase sublimation or by impregnation in solution. In general, the dry impregnation method is preferably used, where the rhenium compound is dissolved in water or in an organic solvent, for example a hydrocarbon, an alcohol or an ether. The quantity of rhenium on the support is adjusted by selecting the concentration of the impregnating solution. When the quantity of rhenium which is to impregnated is higher than that which a solution at its saturation limit will allow, the operation must be carried out several times with intermediate drying steps to eliminate the impregnation solvent, at a temperature of 90° C. to 250° C., for example, preferably 100° C. to 180° C. This enables 0.01 % to 20%, preferably 0.1% to 15%, more advantageously 0.5% to 8% by weight of metallic rhenium, to be introduced. Preferred rhenium compounds are rhenium heptoxide, ammonium perrhenate and perrhenic acid.

After the rhenium impregnation step, a catalyst precursor is obtained, then drying is carried out at a temperature of 90° C. to 250° C., for example, preferably 100° C. to 180° C., followed by calcining at a temperature of more than 750° C. and advantageously at most 1000° C., preferably more than 800° C. and advantageously at most 900° C., in a non reducing gas atmosphere, for example oxygen, nitrogen or argon, oxygen diluted with nitrogen, preferably in air, under static or dynamic conditions, a slow gaseous stream being preferable, however. The amount of moisture in the gaseous stream is preferably kept below 200 ppm (parts per million). However, it is possible to heat in an atmosphere constituted by methane combustion gases or a natural gas in the presence of an excess of air. The duration of this activation treatment is, for example, from 10 minutes to 5 hours or more, after which the precursor obtained is cooled in an atmosphere which is preferably anhydrous. During this calcining treatment, a portion of the gamma alumina is transformed into delta alumina, for example at least 0.5% by weight, preferably 5% to 50% by weight of delta alumina with respect to the starting alumina.

The cesium compound can be introduced into the support using any of the usual methods used in heterogeneous catalysis, for example by solution impregnation. In general, it is preferable to use the dry impregnation method, described above. The cesium compound is dissolved in water. The volume of the solution is less than or at a maximum equal to the volume of the pores of the support. The quantity of cesium on the support is adjusted by selecting the concentration of the impregnation solution. When the quantity which is to be impregnated is higher than that which can be introduced by a solution at its saturation limit, the operation must be carried out several times, with intermediate drying steps to eliminate the impregnation solvent, at a temperature of 90° C. to 250 ° C., for example, preferably 100° C. to 180° C. This enables 0.01% to 5%, preferably 0.1% to 3%, more advantageously 0.2% to 2% by weight of metallic cesium to be introduced. The cesium compound is advantageously a salt such as a halide or a sulphate, preferably a nitrate.

The catalytic composition obtained following the preceding steps is activated by heating between 400° C. and 1000° C., preferably between 500° C. and 900° C., and more preferably between 400° C. and 600° C. If the temperature is increased beyond 750° C., delta alumina formation is observed, but also rhenium is lost due, it appears, to the presence of the cesium. This heating is carried out in a non reducing gas atmosphere, for example: oxygen, nitrogen or argon, oxy Den diluted with nitrogen, preferably in air, under static or dynamic conditions, a slow stream of gas being preferable, however. The amount of moisture of the gas stream is preferably kept below 200 ppm (parts per million). The duration of the activation treatment is, for example, 10 minutes to 5 hours or more, after which the active catalyst obtained is cooled in an atmosphere which is preferably anhydrous. Advantageously, a nitrogen purge is carried out, if necessary, before bringing it into contact with the hydrocarbon-containing feed.

The present invention also concerns a metathesis process using the catalyst described above or obtained by the preparation process described above.

More particularly, the present invention concerns a process for metathesis of an olefinic $C_4$ cut containing 2-butene to produce propylene and isobutene.

When said cut contains diolefins, 1-butene, 2-butene, isobutene and acetylenic impurities, said process comprises, prior to metathesis:

1) selective hydrogenation of the diolefins and acetylenic impurities with isomerisation of 1-butene to 2-butene, to obtain an effluent containing mainly 2-butene and isobutene, and containing practically no diolefins or acetylenic compounds;
2) then separation, by distillation, of an overhead cut containing mainly isobutene and 1-butene not converted in the first step, and a bottom cut containing essentially 2-butene and butane as well as a little residual isobutene;

metathesis being followed by separation of the propylene.

Thus, the present invention proposes a process for treating a $C_4$ hydrocarbon cut containing principally isobutene, n-butenes, butanes, 1,3-butadiene in varying quantities, which includes selective hydrogenation of the diolefins and acetylenic impurities with isomerization of 1-butene to 2-butene, separation of the isobutene by distillation, and metathesis of the 2-butene cut from the preceding step with ethylene, which transforms the 1,3-butadiene and n-butenes to propylene which can, for example, be used for polymerization. In the metathesis step, the use of a rhenium catalyst modified by cesium enables a relatively high residual isobutene content to be tolerated in the 2-butene cut, and thus the severity of the isobutene distillation can be reduced.

The preferred process of the invention is more precisely a process for converting an olefinic $C_4$ cut to isobutene and propylene, said cut containing diolefins, 1-butene, 2-butene, isobutene and acetylenic impurities, said process comprising the following steps carried out successively:

1) selective hydrogenation of the diolefins and acetylenic impurities with isomerization of 1-butene to 2-butene, to obtain an effluent containing mainly 2-butene and isobutene, and containing practically no diolefins or acetylenic compounds, preferably by passing said cut in the liquid phase over a catalyst comprising at least one metal selected from the group formed by nickel, palladium and platinum, deposited on a support, at a temperature of 20–200° C., a pressure of 0.1–5 MPa, a space velocity of 0.5–10 $h^{-1}$, with an $H_2$/diolefins ratio (molar) of 0.5 to 5 and preferably 1 to 3;
2) separation, by distillation, of an overhead cut containing mainly isobutene and 1-butene not converted in the first step, and a bottom cut containing essentially 2-butene and butane as well as a little residual isobutene;
3) metathesis of the 2-butene cut from the preceding step with ethylene, in the presence of a catalyst of the invention as described above, the catalyst containing delta alumina, rhenium and cesium (catalyst preferably having undergone a treatment at a temperature of more than 750° C. and at most 1000° C. to transform a portion of the alumina to delta alumina), at a temperature in the range 0 to 100° C., and at a pressure at least equal to the vapour tension of the reaction mixture at the reaction temperature, so as to obtain an effluent containing propylene, metathesis being followed by separation of propylene.

In the process of the invention, the metathesis reaction is preferably carried out in the liquid phase, in the absence of oxygen, oxygen-containing compounds, nitrogen-containing compounds or sulphur-containing compounds and moisture, at a temperature in the range 0° C. to 100° C., preferably in the range 30° C. to 100° C., and at a pressure of at least the vapour tension of the reaction mixture at the reaction temperature.

The catalyst can be used in a fixed bed. In this case, as it has to be regenerated frequently, it is then necessary to provide at least two reactors in parallel, one being in operation while the other is being regenerated. It is also possible to use a moving catalytic bed system such as that described in French patent FR-A-2 608 595. The catalyst is extracted at regular time intervals from the bottom of the reactor and transferred to a continuous regeneration system, from which the regenerated catalyst is returned to the top of the reactor.

Because of the limits imposed by thermodynamics, the unconverted reactants are fractionated and can be recycled to the metathesis reactor.

The following example illustrates the invention without limiting its scope.

EXAMPLE 1

A metathesis catalyst was prepared by dry impregnation of a gamma alumina with a specific surface area of 180 $m^2/g$ using) an aqueous perrhenic acid solution (rhenium metal content: 54.08% by weight) so as to obtain a catalyst containing about 7% by weight of rhenium. The impregnated solid was dried for 12 hours statically at a temperature of 120° C., then placed in a furnace flushed with a gas constituted by combustion gases from a natural gas burner in the presence of excess air, and where the temperature was gradually increased to 800° C. After a constant stage at this temperature lasting 15 minutes. The catalyst was cooled to ambient temperature in a stream of dry nitrogen.

The catalyst was then modified by incorporating cesium. To this end, it was dry impregnated with an aqueous cesium nitrate solution the concentration of which was such that about 1% of cesium was introduced into the catalyst. When the impregnation operation was completed, the solid was dried for 12 hours under static conditions at a temperature of 120° C., then placed in a furnace flushed with a stream of air, and the temperature was gradually increased to 550° C. After a constant temperature stage lasting 2 hours at this temperature, the catalyst was cooled to ambient temperature in a stream of dry nitrogen. The catalyst obtained contained 6.75% of rhenium and 1% of cesium (in % by weight expressed as the metal).

The metathesis reaction was carried out in a continuous micropilot unit comprising a stainless steel tube reactor charged with 15 g of catalyst as prepared above. The reactant stream was constituted by ethylene and by a $C_4$ cut which had previously undergone selective hydrogenation and hydroisomerization, and from which part of the isobutene had been extracted by distillation. Its composition was as follows:

| Saturated compounds | 37.1% by weight |
|---|---|
| 1-butene | 3.5 |
| Isobutene | 10.5 |
| 2-butene | 43.7 |
| $C_5$ | 5.2 |

The quantity of ethylene introduced was such that the mole ratio of ethylene to 2-butene was equal to 1:1. The total flow rate through the reactor was 25.5 g/h. The temperature was fixed at 60° C. and the pressure was adjusted to 35 bars. After 12 hours of operation, the conversion of 2-butene was 62%, the conversion of 1-butene was 34% and the conversion of isobutene was 15%. These conversions remained stable for 80 hours, then started to decrease. In an industrial operation, it would then be necessary to regenerate the catalyst, and the operating cycle duration would be 80 hours.

What is claimed is:

1. A process for preparing a catalyst comprising:
   forming a catalyst precursor based on gamma alumina and rhenium,
   calcining said precursor by heating it to more than 750° C. in a non-reducing gas atmosphere, and
   activating the catalyst by heating it to 400° C.–600° C. in a non-reducing gas atmosphere.

2. A preparation process according to claim 1, wherein said precursor also contains cesium.

3. A preparation process according to claim 1, wherein after said calcining, said precursor is impregnated with a cesium compound, dried, and then subjected to said heating to 400° C.–600° C.

4. A preparation process according to claim 3, wherein the cesium compound used to impregnate the catalyst is selected from the group consisting of cesium halides, sulphates and cesium nitrates.

5. A process according to claim 3, wherein the resultant catalyst comprises a porous alumina-based support containing at least 75 wt % alumina which is impregnated with 0.01–20 wt % rhenium, and 0.01–5 wt % cesium.

6. A process according to claim 3, wherein following cesium impregnation with a cesium compound, the catalyst precursor is dried at a temperature of 90–250° C., and, optionally, the cesium impregnation and drying steps are repeated.

7. A process according to claim 3, wherein following impregnation with a cesium compound, the catalyst precursor contains at least 0.5 wt % delta alumina, 0.01–20 wt % rhenium, and 0.01–5% cesium.

8. A process according to claim 3, wherein following impregnation with a cesium compound, the catalyst precursor contains at least 0.5 wt % delta alumina, 0.1–15 wt % rhenium, and 0.1–3% cesium.

9. A process according to claim 3, wherein following impregnation with a cesium compound, the catalyst precursor contains at least 0.5 wt % delta alumina, 0.5–8 wt % rhenium, and 0.2–2% cesium.

10. A preparation process according to claim 1, in which said precursor is formed from a porous alumina-based support comprising at least 75% by weight of alumina and having a surface area of at least 10 $m^2/g$ and a pore volume of at least 0.1 ml/g.

11. A preparation process according to claim 1, wherein said precursor is formed by impregnating a porous-alumina-based support with a rhenium compound selected from the group consisting of rhenium heptoxide, ammonium perrhenate and perrhenic acid.

12. A process according to claim 1, wherein said catalyst precursor comprises a porous alumina-based support containing at least 75 wt % alumina which is impregnated with rhenium.

13. A process according to claim 1, wherein said catalyst precursor is prepared by impregnating a porous alumina-based support with a solution containing a rhenium compound, drying the catalyst precursor at a temperature of 90–250° C., and optionally repeating the impregnating and drying steps.

14. A preparation process according to claim 13, wherein, after said calcining, said precursor is impregnated with a cesium compound, dried at a temperature of 90–250° C., optionally, the cesium impregnation and drying steps are repeated, and then subjected to said heating to 400° C.–600° C., and the resultant catalyst contains at least 0.5 wt % delta alumina, 0.01–20 wt % rhenium, and 0.01–5% cesium.

15. A process according to claim 1, wherein calcining is performed at a temperature of more than 750° C. and at most 1000° C.

16. A process according to claim 15, wherein calcining is performed at a temperature of more than 800° C. and at most 1000° C.

17. A process according to claim 1, wherein during calcining, 5–50 wt % of the alumina of said catalyst precursor is transformed into delta alumina.

18. A process according to claim 1, wherein following calcining, the catalyst precursor contains at least 0.5 wt % delta alumina and 0.01–20 wt % rhenium.

19. A process according to claim 18, wherein the catalyst precursor contains 0.1–15 wt % rhenium.

20. A process according to claim 18, wherein the catalyst precursor contains 0.5–8 wt % rhenium.

* * * * *